United States Patent
Someya et al.

(10) Patent No.: US 11,440,869 B2
(45) Date of Patent: Sep. 13, 2022

(54) COMPOUND, RESIN PRECURSOR, CURED PRODUCT, OPTICAL ELEMENT, OPTICAL SYSTEM, INTERCHANGEABLE LENS FOR CAMERA, OPTICAL DEVICE, CEMENTED LENS, AND PRODUCTION METHOD FOR CEMENTED LENS

(71) Applicant: NIKON CORPORATION, Tokyo (JP)

(72) Inventors: Yoshihiro Someya, Yamato (JP); Masayuki Shijo, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 267 days.

(21) Appl. No.: 16/831,292

(22) Filed: Mar. 26, 2020

(65) Prior Publication Data

US 2020/0223781 A1    Jul. 16, 2020

Related U.S. Application Data

(63) Continuation of application No. PCT/JP2018/014934, filed on Apr. 9, 2018.

(30) Foreign Application Priority Data

Oct. 3, 2017 (JP) .............................. JP2017-193446

(51) Int. Cl.
*C07C 69/54* (2006.01)
*C07C 69/602* (2006.01)
(Continued)

(52) U.S. Cl.
CPC ............ *C07C 69/54* (2013.01); *C07C 69/602* (2013.01); *C08F 220/20* (2013.01);
(Continued)

(58) Field of Classification Search
CPC ...... C07C 69/54; C07C 69/602; C08F 220/20; C08F 220/24; C08F 222/1025; G02B 3/00; G02B 7/14; G02B 1/041
See application file for complete search history.

(56) References Cited

U.S. PATENT DOCUMENTS 5,349,035 A * 9/1994 Brand ................. C08F 220/306
526/292.3
5,442,022 A   8/1995 Keita et al.
(Continued)

FOREIGN PATENT DOCUMENTS

CN        104508516 A    4/2015
JP        61-134701      6/1986
(Continued)

OTHER PUBLICATIONS

International Search Report dated Oct. 7, 2018, in corresponding Patent Application No. PCT/JP2018/014934.
(Continued)

*Primary Examiner* — James C. Jones

(57) ABSTRACT

A compound expressed in the following formula (1)

(1)

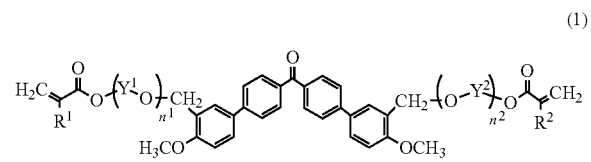

(where $R^1$ and $R^2$ independently denote a hydrogen atom or a methyl group, $Y^1$ and $Y^2$ independently denote an alkylene
(Continued)

group having a carbon number of 1 to 9, and $n^1$ and $n^2$ independently denote an integer of 0 to 3).

23 Claims, 5 Drawing Sheets

(51) Int. Cl.
*C08F 220/20* (2006.01)
*C08F 220/24* (2006.01)
*G02B 3/00* (2006.01)
*C08F 222/10* (2006.01)
*G02B 7/14* (2021.01)

(52) U.S. Cl.
CPC ...... *C08F 220/24* (2013.01); *C08F 222/1025* (2020.02); *G02B 3/00* (2013.01); *G02B 7/14* (2013.01)

(56) References Cited

U.S. PATENT DOCUMENTS

| | | | |
|---|---|---|---|
| 5,741,831 | A | 4/1998 | Keita et al. |
| 2009/0054547 | A1 | 2/2009 | Berit-Debat et al. |

FOREIGN PATENT DOCUMENTS

| | | |
|---|---|---|
| JP | 6-500811 | 1/1994 |
| JP | 6-32843 | 2/1994 |
| JP | 7-238120 | 9/1995 |
| JP | 8-208776 | 8/1996 |
| JP | 8-325337 | 12/1996 |
| JP | 2007-327040 | 12/2007 |
| JP | 2009-57560 | 3/2009 |
| JP | 2016-95542 | 5/2016 |
| WO | WO2014/021355 | 2/2014 |

OTHER PUBLICATIONS

Chinese Office Action dated Jun. 8, 2021, issued in Chinese Application No. 201880060254.9.
Office Action, dated Feb. 28, 2022, in counterpart Chinese Patent Application No. 201880060254.9 (10 pp.).
English Translation of Office Action, dated Jun. 8, 2021, in counterpart Chinese Patent Application No. 201880060254.9 (7 pp.).
Extended European Search Report, dated May 28, 2021, in corresponding European Patent Application No. 18864437.1 (6 pp.).
Office Action, dated Nov. 15, 2021, in corresponding Chinese Patent Application No. 201880060254.9 (8 pp.).

* cited by examiner

COMPOUND, RESIN PRECURSOR, CURED PRODUCT, OPTICAL ELEMENT, OPTICAL SYSTEM, INTERCHANGEABLE LENS FOR CAMERA, OPTICAL DEVICE, CEMENTED LENS, AND PRODUCTION METHOD FOR CEMENTED LENS

CROSS-REFERENCE TO RELATED APPLICATIONS

This application is a Continuation Application, under 35 U.S.C. § 111(a), of International Patent Application No. PCT/JP2018/014934, filed on Apr. 9, 2018, which claims foreign priority benefit of Japanese Patent Application No. 2017-193446 filed on Oct. 3, 2017 in the Japanese Intellectual Property Office, the contents of both of which are incorporated herein by reference.

FIELD OF THE INVENTION

The present invention relates to a compound, a resin precursor, a cured product, an optical element, an optical system, an interchangeable lens for camera, an optical device, a cemented lens, and a production method for cemented lens.

DESCRIPTION OF THE RELATED ART

For example, Patent Document 1 discloses a cemented lens obtained by bonding an object-side lens having negative power and an image-side lens having positive power to each other using a resin adhesive layer. The resin adhesive layer used in such a cemented lens is necessarily formed of a material having a high θgF value in order to satisfactorily correct chromatic aberration.

CITATION LIST

Patent Documents

Patent Document 1: Japanese Unexamined Patent Application No. 2016-095542

SUMMARY OF THE INVENTION

A first aspect of the present invention is a compound expressed in the following formula (1)

A second aspect of the present invention is a resin precursor including:
 the compound described above; and
 a curable composition.

A third aspect of the present invention is a cured product obtained by curing the resin precursor described above.

A fourth aspect of the present invention is an optical element obtained by using the cured product described above.

A fifth aspect of the present invention is an optical system including the optical element described above.

A sixth aspect of the present invention is an interchangeable lens for camera including the optical system described above.

A seventh aspect of the present invention is an optical device including the optical system described above.

An eighth aspect of the present invention is a cemented lens including a first lens element and a second lens element bonded by interposing the cured product described above.

A ninth aspect of the present invention is a production method for cemented lens, including:
 an adjoining step of adjoining a first lens element and a second lens element by interposing the resin precursor described above; and
 a bonding step of bonding the first lens element and the second lens element by curing the resin precursor described above.

DESCRIPTION OF EMBODIMENTS

Figure 1:
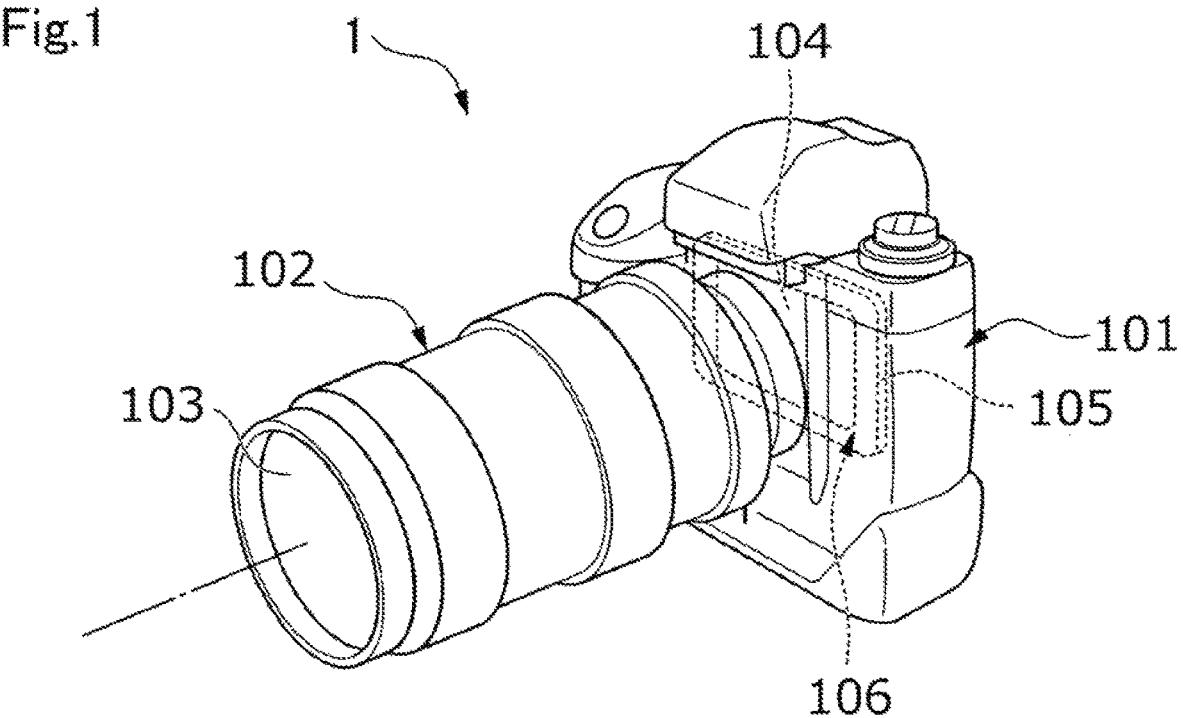
FIG. 1 is a perspective view illustrating an example in which an optical device according to a present embodiment is an imaging device.

Hereinafter, a mode for carrying out the present invention (hereinafter, simply referred to as "the present embodi-

[Chemical Expression 1]

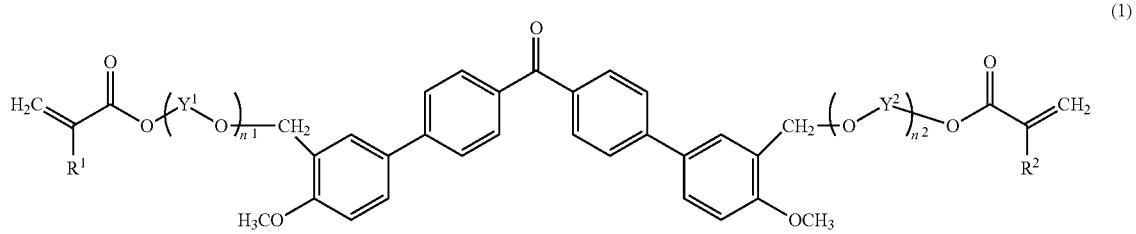

(1)

(where $R^1$ and $R^2$ independently denote a hydrogen atom or a methyl group, $Y^1$ and $Y^2$ independently denote an alkylene group having a carbon number of 1 to 9, and $n^1$ and $n^2$ independently denote an integer of 0 to 3).

ment") will be described in detail. The following present embodiments are examples for describing the present invention, and are not intended to limit the present invention to the following contents. Note that, in the drawings, the positional relationship such as up, down, left, and right is based on the positional relationship shown in the drawings unless specified otherwise. In addition, the dimensional ratios in the drawings are not limited to those illustrated. Furthermore, acrylate and methacrylate may be collectively referred to as "(meth)acrylate" in some cases.

The compound according to the present embodiment is a compound expressed in the following Formula (1).

[Chemical Expression 2]

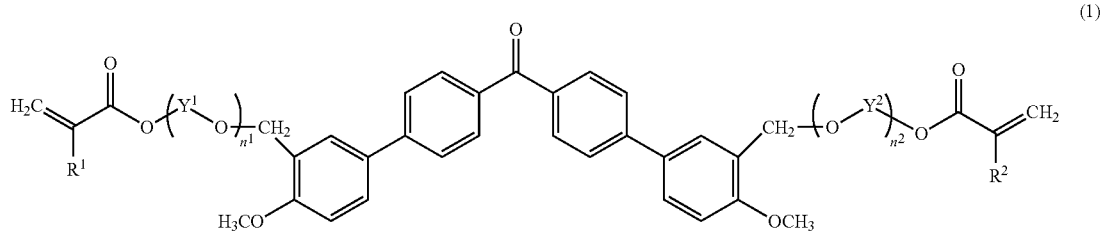

(1)

(where $R^1$ and $R^2$ independently denote a hydrogen atom or a methyl group, $Y^1$ and $Y^2$ independently denote an alkylene group having a carbon number of 1 to 9, and $n^1$ and $n^2$ independently denote an integer of 0 to 3).

The compound expressed in the Formula (1) (hereinafter, referred to as Compound (1) in some cases) is a novel compound. The Compound (1) may be suitably used as one of the components of a resin precursor which is a material for an optical element or the like. In addition, by using such a compound, it is possible to obtain an optical element having an excellent θgF value. In particular, even when the Compound (1) is used as a material of a multilayered optical element (cemented lens) obtained by combining a concave lens and a convex lens, it can be expected to exhibit excellent optical properties with a thin shape and provide an excellent chromatic aberration correction effect. Note that the θgF value is a value expressed as "$(n_g-n_F)/(n_F-n_C)$", where $n_C$, $n_F$, and $n_g$ denote refractive indices for the C-line (wavelength of 656.3 nm), F-line (486.1 nm), and g-line (435.8 nm), respectively.

<Compound (1)>

Hereinafter, the structure of the Compound (1) will be described.

$R^1$ and $R^2$ independently denote a hydrogen atom or a methyl group.

$Y^1$ and $Y^2$ independently denote an alkylene group having a carbon number of 1 to 9. The alkylene group may have either a linear structure or a branched structure. The carbon number is preferably set to 1 to 5, more preferably 2 to 5, and furthermore preferably 2 to 4, from the viewpoint of suppressing precipitation of insoluble components, stability, or the like in preparation of a resin precursor or the like.

Specifically, the alkylene groups $Y^1$ and $Y^2$ may include, for example, a methylene group, an ethylene group, a propylene group, an isopropylene group, an n-butylene group, an isobutylene group, a tert-butylene group, an n-pentylene group, an isopentylene group, a neopentylene group, an n-hexylene group, an isohexylene group, a neohexylene group, a heptylene group, an octylene group, a nonylene group, or the like. Among them, from the viewpoint of suppressing precipitation of insoluble components, stability, or the like in preparation of the resin precursor or the like, the methylene group, the ethylene group, the propylene group, the isopropylene group, the n-pentylene group, the isopentylene group, and the neopentylene group are preferable, and the ethylene group, the propylene group, the n-butylene group, the n-pentylene group, and the neopentylene group are more preferable.

$n^1$ and $n^2$ independently denote an integer of 0 to 3. The numbers $n^1$ and $n^2$ are preferably set to "1" or "2", and more preferably "1", from the viewpoint of suppressing precipitation of insoluble components in preparation of the resin precursor or the like and being easily obtainable.

<Resin Precursor>

According to the present embodiment, a resin precursor containing the Compound (1) and the curable composition can be obtained. The resin precursor can be suitably used as a resin precursor for optical materials. When the resin precursor is used as an optical material, it is desirable that the resin precursor stably exists in a liquid state under a normal temperature and a normal pressure. From such a viewpoint, the resin precursor according to the present embodiment is preferably in a liquid state under a normal temperature and a normal pressure. In addition, by using the curable composition described below in combination with the Compound (1), it is possible to effectively suppress precipitation of insoluble components and easily prepare a stable liquid composition.

The curable composition may be either a photocurable type or a thermocurable type. Preferably, the curable composition is a photocurable composition. For example, when a lot of (meth)acrylate-based compounds are contained, the curable composition is preferably a photocurable composition.

The curable composition is not particularly limited. For example, the curable composition may include at least one selected from a group consisting of a fluorine-containing (meth)acrylate compound, a (meth)acrylate compound having a fluorene structure, and a di(meth)acrylate compound. By using such a component in combination with the Compound (1), it is possible to effectively suppress precipitation of insoluble components and easily prepare a stable liquid composition. As a result, it is possible to suppress generation of a precipitate during storage and eliminate necessity of operation for removing the precipitate before using the composition. In addition, it is possible to obtain a homogeneous cured product having a low refractive index and a high dispersion.

The fluorine-containing (meth)acrylate compound may include, for example, monofunctional, bifunctional, trifunctional, or more functional fluorine-containing (meth)acrylate. Among them, the bifunctional fluorine-containing (meth)acrylate is preferable because it is easily obtainable. The bifunctional fluorine-containing (meth)acrylate may include the compound expressed in the following Formula (2).

[Chemical Expression 3]

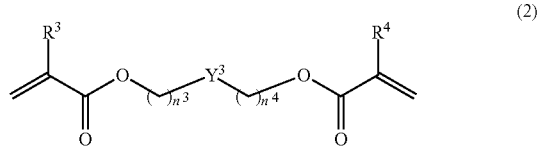

(2)

(where $R^3$ and $R^4$ independently denote a hydrogen atom or a methyl group, $n^3$ and $n^4$ independently denote an integer of 1 to 12, $Y^3$ denotes a perfluoroalkylene group having a carbon number of 2 to 12 or —$(CF_2$—O—$CF_2)_z$-, and "z" denotes an integer of 1 to 4).

$R^3$ and $R^4$ independently denote a hydrogen atom or a methyl group. Among them, $R^3$ and $R^4$ are preferably hydrogen atoms.

$n^3$ and $n^4$ independently denote an integer of 1 to 12. The numbers $n^3$ and $n^4$ are preferably set to an integer of 1 to 6, more preferably an integer of 1 to 4, and furthermore preferably an integer of 1 or 2 from the viewpoint of suppressing precipitation of insoluble components in preparation of the resin precursor or the like and being easily obtainable.

$Y^3$ denotes a perfluoroalkylene group having a carbon number of 2 to 12 or —$(CF_2$—O—$CF_2)_z$-, and "z" denotes an integer of 1 to 4. The perfluoroalkylene group may have either a linear structure or a branched structure. The perfluoroalkylene group preferably includes —$(CF_2)$—, —$(CF_2CF_2)$—, —$(CF_2CF_2CF_2)$—, or —$(CF_2CF_2CF_2CF_2)$—. The number "z" is preferably an integer of 1 to 3, and more preferably an integer of 1 or 2.

Specifically, the bifunctional fluorine-containing (meth)acrylate compound may include, for example, 1,4-di(meth)acryloyloxy-2,2,3,3-tetrafluorobutane, 1,6-di(meth)acryloyloxy-3,3,4,4-tetrafluorohexane, 1,6-di(meth)acryloyloxy-3,3,4,4-tetrafluorohexane, 1,6-di(meth)acryloyloxy-2,2,3,3,4,4,5,5-octafluorohexane, 1,8-di(meth)acryloyloxy-3,3,4,4,5,5,6,6-octafluorooctane, 1,8-di(meth)acryloyloxy-2,2,3,3,4,4,5,5,6,6,7,7-dodecafluorooctane, 1,9-di(meth)acryloyloxy-2,2,3,3,4,4,5,5,6,6,7,7,8,8-tetradecafluorononane, 1,10-di(meth)acryloyloxy-2,2,3,3,4,4,5,5,6,6,7,7,8,8,9,9-hexadecafluorodecane, 1,12-di(meth)acryloyloxy-2,2,3,3,4,4,5,5,6,6,7,7,8,8,9,9,10,10,11,11-icosafluorododecane, or the like. In addition, ethylene oxide-modified fluorinated bisphenol-A di(meth)acrylate, propylene oxide-modified fluorinated bisphenol-A di(meth)acrylate, or the like may also be used as the bifunctional fluorine-containing (meth)acrylate.

Among them, the bifunctional fluorine-containing (meth)acrylate compound preferably includes 1,6-di(meth)acryloyloxy-2,2,3,3,4,4,5,5-octafluorohexane, and more preferably the compound expressed in the following Formula (2-1) (1,6-di-acryloyloxy-2,2,3,3,4,4,5,5-octafluorohexane).

[Chemical expression 4]

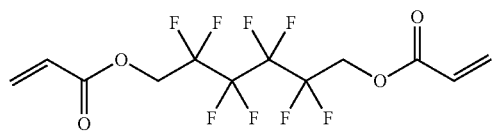

(2-1)

The content of the fluorine-containing (meth)acrylate compound in the resin precursor is not particularly limited. However, from the viewpoint of the optical properties such as the Abbe number, mutual solubility with the Compound (1), and the like, the total amount of the fluorine-containing (meth)acrylate compound is preferable set to 20 to 50 mass %, more preferably 30 to 45 mass % and furthermore preferably 35 to 42 mass %.

The (meth)acrylate compound having the fluorene structure may include, for example, a monofunctional (meth)acrylate compound having a fluorene structure, a bifunctional (meth)acrylate compound having a fluorene structure, and trifunctional or more functional (meth)acrylate compounds having a fluorene structure. Among them, the bifunctional (meth)acrylate compound having the fluorene structure is preferably because it is easily obtainable. As a specific example of such a compound, the compound expressed in the following Formula (3) or the compound expressed in the following Formula (4) may be included.

[Chemical Expression 5]

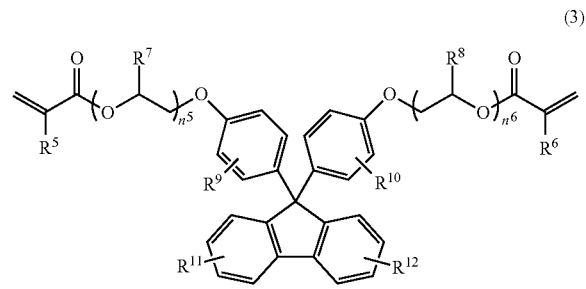

(3)

(where $R^5$ and $R^6$ independently denote a hydrogen atom or a methyl group, $R^7$ and $R^8$ independently denote a hydrogen atom, a methyl group, or an ethyl group, $R^9$, $R^{10}$, $R^{11}$, and $R^{12}$ independently denote a hydrogen atom, a fluorine atom, an alkyl group having a carbon number of 1 to 6, or a phenyl group in which the hydrogen atom may be substituted with a fluorine atom or an alkyl group having a carbon number of 1 to 6, and $n^5$ and $n^6$ independently denote an integers of 0 to 3).

[Chemical Expression 6]

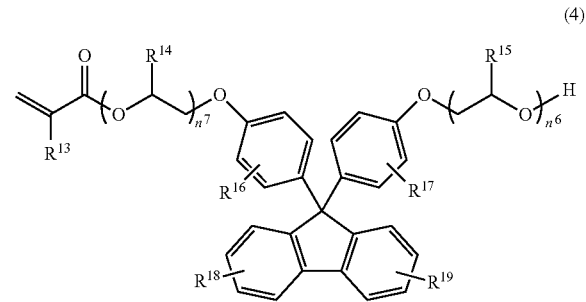

(4)

(where $R^{13}$ denotes a hydrogen atom or a methyl group, $R^{14}$ and $R^{15}$ independently denote a hydrogen atom, a methyl group, or an ethyl group, $R^{16}$, $R^{17}$, $R^{18}$, and $R^{19}$ independently denote a hydrogen atom, a fluorine atom, an alkyl group having a carbon number of 1 to 6, or a phenyl group in which the hydrogen atom may be substituted with a fluorine atom or an alkyl group having a carbon number of 1 to 6, and $n^7$ and $n^8$ independently denote an integer of 0 to 3).

The Formula (3) will be described.

$R^5$ and $R^6$ independently denote a hydrogen atom or a methyl group. Among them, the hydrogen atom is preferable.

$R^7$ and $R^8$ independently denote a hydrogen atom, a methyl group, or an ethyl group. Among them, the hydrogen atom is preferable because it is easily obtainable.

$R^9$, $R^{10}$, $R^{11}$, and $R^{12}$ independently denote a hydrogen atom, a fluorine atom, an alkyl group having a carbon number of 1 to 6, or a phenyl group in which the hydrogen atom may be substituted with a fluorine atom or an alkyl group having a carbon number of 1 to 6.

The alkyl group having a carbon number of 1 to 6 may have either a linear, branched, or cyclic structure. The linear or branched structure is preferable because they are easily obtainable. Specifically, the alkyl group having a carbon number of 1 to 6 may include, for example, a methyl group, an ethyl group, a propyl group, an isopropyl group, an n-butyl group, an isobutyl group, a tert-butyl group, an n-pentyl group, an isopentyl group, a neopentyl group, an n-hexyl group, an isohexyl group, a neohexyl group, a cyclopropyl group, a cyclobutyl group, a cyclopentyl group, a cyclohexyl group, or the like. Among them, the methyl group or the ethyl group is preferable.

The phenyl group in which the hydrogen atom may be substituted with a fluorine atom or an alkyl group having a carbon number of 1 to 6 is obtained by substituting a part or all of the hydrogen atoms of the phenyl group with the fluorine atom or the alkyl group having a carbon number of 1 to 6. Such an alkyl group having a carbon number of 1 to 6 preferably includes a methyl group or an ethyl group because they are easily obtainable.

$n^5$ and $n^6$ independently denote integers of "0" to "3". Among them, from the viewpoints of high hardness or transparency and excellent optical properties, the numbers $n^5$ and $n^6$ are preferably set to an integer of "0" to "2", more preferably "0" or "1", furthermore preferably "1".

The Formula (4) will be described.

$R^{13}$ denotes a hydrogen atom or a methyl group. Among them, $R^{13}$ is preferably a hydrogen atom.

$R^{14}$ and $R^{15}$ independently denote a hydrogen atom, a methyl group, or an ethyl group. Among them, $R^{14}$ and $R^{15}$ are preferably hydrogen atoms because they are easily obtainable.

$R^{16}$, $R^{17}$, $R^{18}$, and $R^{19}$ independently denote a hydrogen atom, a fluorine atom, an alkyl group having a carbon number of 1 to 6, or a phenyl group in which the hydrogen atom may be substituted with a fluorine atom or an alkyl group having a carbon number of 1 to 6.

The alkyl group having a carbon number of 1 to 6 may have either a linear, branched, or cyclic structure. The linear or branched structure is preferable because they are easily obtainable. Specifically, the alkyl group having a carbon number of 1 to 6 may include, for example, a methyl group, an ethyl group, a propyl group, an isopropyl group, an n-butyl group, an isobutyl group, a tert-butyl group, an n-pentyl group, an isopentyl group, a neopentyl group, an n-hexyl group, an isohexyl group, a neohexyl group, a cyclopropyl group, a cyclobutyl group, a cyclopentyl group, a cyclohexyl group, or the like. Among them, the methyl group or the ethyl group is preferable.

The phenyl group in which the hydrogen atom may be substituted with a fluorine atom or an alkyl group having a carbon number of 1 to 6 is obtained by substituting a part or all of the hydrogen atoms of the phenyl group with the fluorine atom or the alkyl group having a carbon number of 1 to 6. Such an alkyl group having a carbon number of 1 to 6 preferably includes a phenyl group, a methylphenyl group, or an ethylphenyl group because they are easily obtainable.

$n^7$ and $n^8$ independently denote integers of "0" to "3". Among them, from the viewpoints of high hardness or transparency and excellent optical properties, the numbers $n^7$ and $n^8$ are preferably set to an integer of "0" to "2", more preferably "0" or "1", furthermore preferably "1".

Specifically, the (meth)acrylate compound having a fluorene structure preferably includes the compound expressed in the following Formula (3-1) or the compound expressed in the following Formula (4-1), and more preferably the compound expressed in the following Formula (3-1) (9,9-bis[4-(2-acryloyloxyethoxy)phenyl]fluorene).

[Chemical Expression 7]

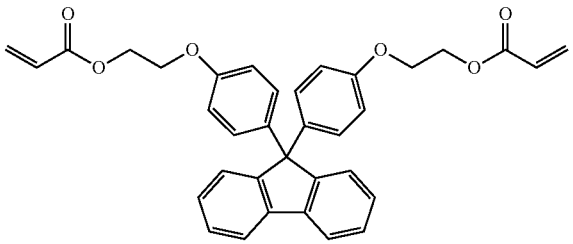

(3-1)

[Chemical Expression 8]

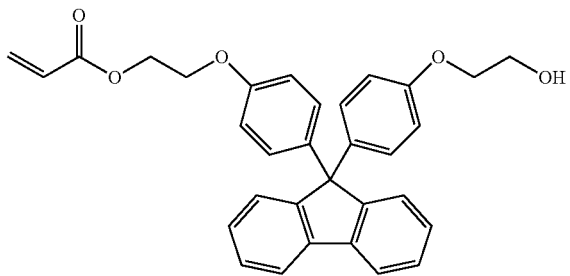

(4-1)

The content of the (meth)acrylate compound having the fluorene structure in the resin precursor is not particularly limited. However, the total amount of the (meth)acrylate compound having the fluorene structure is preferably set to 20 to 50 mass %, more preferably 25 to 40 mass %, and furthermore preferably 26 to 35 mass % from the viewpoint of suppressing white turbidness or precipitation of insoluble components.

The di(meth)acrylate compound may include a compound having two (meth)acrylate structures other than those described above. Specifically, the di(meth)acrylate compound may include, for example, 2-ethyl, 2-butyl-propanediol (meth)acrylate, 1,3-butylene glycol di(meth)acrylate, 1,6-hexanediol di(meth)acrylate, 1,9-nonanediol (meth)acrylate, 1,10-decanedioldi(meth)acrylate, neopentyl glycol di(meth)acrylate, dipropylene glycol di(meth)acrylate, glycerol di(meth)acrylate, ethylene oxide-modified neopentyl glycol di(meth)acrylate, propylene oxide-modified neopentyl glycol di(meth)acrylate, ethylene oxide-modified bisphenol-A di(meth)acrylate, propylene oxide-modified bisphenol-A di(meth)acrylate, ethylene oxide/propylene oxide-modified bisphenol-A di(meth)acrylate, butylethyl propanediol di(meth)acrylate, or the like.

Among the di(meth)acrylate compounds, the aliphatic di(meth)acrylate is preferable from the viewpoint of mutual solubility with the Compound (1), and the like. Among them, 2-ethyl, 2-butyl-propanediol (meth)acrylate, 1,3-butylene glycol di(meth)acrylate, and 1,6-hexanediol di(meth) acrylate are preferable, and 1,6-hexanediol diacrylate (AHDN) is more preferable. Since the aliphatic di(meth) acrylate has high mutual solubility with the Compound (1) due to its chemical structure, it is possible to maintain a stable liquid state. As a result, it is possible to obtain a liquid resin precursor containing the Compound (1) at a high concentration. The resin precursor containing the Compound (1) at a high concentration can more effectively exhibit the effects of the optical properties when it is used as an optical material.

The content of the di(meth)acrylate compound in the resin precursor is not particularly limited, but from the viewpoint of mutual solubility with the Compound (1), and the like, the total amount of the di(meth)acrylate compound is preferably set to 10 to 80 mass %, more preferably 20 to 60 mass %, and furthermore preferably 35 to 50 mass %.

The curable composition according to the present embodiment may contain any component other than those described above. For example, the curable composition may contain monofunctional (meth)acrylate, trifunctional (meth)acrylate, tetrafunctional (meth)acrylate, or the like. By using them in combination, it is possible to adjust the hardness, transparency, and optical properties of the resin. Among them, the monofunctional (meth)acrylate is preferable from the viewpoint of improving the mutual solubility with the Compound (1).

The monofunctional (meth)acrylate may include, for example, methyl (meth)acrylate, ethyl (meth)acrylate, butyl (meth)acrylate, isodecyl (meth)acrylate, lauryl (meth)acrylate, tridecyl (meth)acrylate, acethyl (meth)acrylate, stearyl (meth)acrylate, tert-butyl (meth)acrylate, 2-ethylhexyl (meth)acrylate, 2-hydroxy butyl (meth)acrylate, 2-hydroxy ethyl (meth)acrylate, 2-hydroxypropyl (meth)acrylate, 3-methoxybutyl (meth)acrylate, diethylaminoethyl (meth) acrylate, phenoxy polyethylene glycol (meth)acrylate, isostearyl (meth)acrylate, paracumyl phenoxy ethylene glycol (meth)acrylate, dimethylaminoethyl (meth)acrylate, 2-ethylhexyl carbitol (meth)acrylate, butoxyethyl (meth) acrylate, ethoxydiethylene glycol (meth)acrylate, lauroxy polyethylene glycol (meth)acrylate, polyethylene glycol (meth)acrylate, methoxydipropylene glycol acrylate, methoxytripropylene glycol acrylate, ethoxydipropylene glycol acrylate, ethoxytripropylene glycol acrylate, polypropylene glycol (meth)acrylate, acryloxy polyethylene glycol (meth)acrylate, stearoxy polyethylene glycol (meth)acrylate, octoxypolyethylene glycol-polypropylene glycol (meth)acrylate, poly(propylene glycol-tetramethylene glycol) (meth)acrylate, poly(ethylene glycol-tetramethylene glycol) (meth)acrylate, methoxypolyethylene glycol (meth) acrylate, methoxypolypropylene glycol (meth)acrylate, benzyl (meth)acrylate, or the like. Among them, the methoxytripropylene glycol acrylate and the ethoxytripropylene glycol acrylate are preferable from the structural viewpoint of mutual solubility with the Compound (1) or the like.

The trifunctional (meth)acrylate may include, for example, tris(acryloxyethyl) isocyanurate, tris(methacryloxyethyl) isocyanurate, epichlorohydrin-modified glycerol tri(meth)acrylate, ethylene oxide-modified glycerol tri (meth)acrylate, propylene oxide-modified glycerol tri(meth) acrylate, caprolactone-modified trimethylolpropane tri (meth)acrylate, ethylene oxide-modified trimethylolpropane tri(meth)acrylate, propylene oxide-modified trimethylolpropane tri(meth)acrylate, pentaerythritol tri(meth)acrylate, trimethylolpropane tri(meth)acrylate, or the like. Among them, the pentaerythritol tri(meth)acrylate is preferable from the structural viewpoint of mutual solubility with the Compound (1) or the like.

The tetrafunctional (meth)acrylate may include, for example, pentaerythritol tetra(meth)acrylate, dipentaerythritol hydroxy penta(meth)acrylate, ditrimethylolpropane tetra(meth)acrylate, or the like. Among them, the dipentaerythritol hydroxy penta(meth)acrylate is preferable from the structural viewpoint of mutual solubility with the Compound (1) or the like.

When the resin precursor according to the present embodiment is photocurable, the resin precursor may further contain a photopolymerization initiator. The photopolymerization initiator is not particularly limited as long as it can initiate polymerization of the monomer component by light irradiation. Any photopolymerization initiator used for resin photocuring and known in the art may be used. The light used for light irradiation may be appropriately selected depending on the photopolymerization initiator to be used, and may generally include visible light, ultraviolet light, electron beams, or the like.

The content of the photopolymerization initiator depends on the type of the component to be used or the type of the light to be irradiated. Preferably, the content of the photopolymerization initiator is generally set to 0.1 to 5 mass %.

As the photopolymerization initiator, for example, a phosphine-based or acetophenone-based photopolymerization initiator is preferable from the viewpoint of reactivity. As the phosphine-based photopolymerization initiator, bis(2-4-6-trimethylbenzoyl)-phenylphosphine oxide, 2,4,6-trimethylbenzoyl-diphenyl-phosphine oxide, or the like is preferable. As the acetophenone-based photopolymerization initiator, alkylphenyl ketones having a hydroxyl group at the α-position are preferable, and 1-hydroxy-cyclohexyl-phenyl-ketone, 2-hydroxy-2-methyl-1-phenyl-propan-1-one, or the like is more preferable from the viewpoint of suppressing yellowing of the resin in addition to the reactivity.

The resin precursor according to the present embodiment may further contain a photostabilizer. Any photostabilizer known in the art may be used. Preferably, the photostabilizer may include, for example, a hindered amine-based material such as bis(2,2,6,6-tetramethyl-4-piperidyl) sebacate, bis(1, 2,2,6,6-pentamethyl-4-biperidyl) sebacate, or methyl 1,2,2, 6,6-pentamethyl-4-piperidyl sebacate.

The resin precursor according to the present embodiment may further contain a polymerization inhibitor. Any polymerization inhibitor known in the art may be used. Preferably, the polymerization inhibitor may include, for example, hydroquinones such as p-benzoquinone, hydroquinone, hydroquinone monomethyl ether, or 2,5-diphenylparabenzoquinone; substituted catechols such as T-butylcatechol; amines such as phenothiazine or diphenylamine; N-oxy radicals such as tetramethylpiperidinyl N-oxy radical (TEMPO); nitrosobenzene; picric acid; molecular oxygen; sulfur, or the like. Among them, the hydroquinones, phenothiazines, and N-oxy radicals are more preferable from the viewpoint of versatility or polymerization suppression.

The resin precursor according to the present embodiment may further contain an ultraviolet absorber. Any ultraviolet absorber known in the art may be used. Preferably, the ultraviolet absorber may include, for example, 2-(2-hydroxy-5-t-octylphenyl)-2H-benzotriazole, or the like. A better effect can be expected when the ultraviolet absorber is used in combination with the photostabilizer.

As a suitable combination of the components described above, the curable composition used in combination with the Compound (1) preferably includes a fluorine-containing (meth)acrylate compound or a (meth)acrylate compound having a fluorene structure and di(meth)acrylate compound, more preferably a fluorine-containing (meth)acrylate compound and di(meth)acrylate compound, and furthermore preferably an fluorine-containing aliphatic (meth)acrylate compound and aliphatic di(meth)acrylate compound.

A specific combination of the components as the curable composition preferably includes at least any one selected from a group consisting of 9,9-bis[4-(2-acryloyloxyethoxy) phenyl]fluorene, methoxytripropylene glycol acrylate, 1,6-di(meth)acryloyloxy-2,2,3,3,4,4,5,5-octafluorohexane, 1-hydroxy-cyclohexyl-phenyl-ketone, bis(2-4-6-trimethyl-benzoyl)-phenylphosphine oxide, bis(1,2,2,6,6-pentamethyl-4-biperidyl) sebacate, methyl 1,2,2,6,6-pentamethyl-4-piperidyl sebacate, 2-(2-hydroxy-5-t-octylphenyl)-2H-benzotriazole, and 1,6-hexanediol diacrylate.

Among them, the combination of the components as the curable composition more preferably includes at least any one selected from a group consisting of 1,6-di(meth)acryloyloxy-2,2,3,3,4,4,5,5-octafluorohexane, 9,9-bis[4-(2-acryloyloxyethoxy)phenyl]fluorene, and 1,6-hexanediol diacrylate because it is possible to effectively suppress precipitation of insoluble components and easily prepare a stable liquid composition. In addition, the combination of the components as the curable composition further preferably includes at least two selected from a group consisting of 1,6-di(meth)acryloyloxy-2,2,3,3,4,4,5,5-octafluorohexane, 9,9-bis[4-(2-acryloyloxyethoxy)phenyl]fluorene, and 1,6-hexanediol diacrylate, and furthermore preferably includes 1,6-di(meth)acryloyloxy-2,2,3,3,4,4,5,5-octafluorohexane, 9,9-bis[4-(2-acryloyloxyethoxy)phenyl]fluorene, and 1,6-hexanediol diacrylate. By using such a component in combination with the Compound (1), it is possible to more easily prepare a liquid composition having high stability under a normal temperature condition.

The content of the Compound (1) in the resin precursor is not particularly limited, but it is preferably set to 10 to 50 mass % from the viewpoint of maintaining high stability in a liquid state. In addition, from the viewpoint described above, the content of the Compound (1) in the resin precursor may be set to 10 to 30 mass %, 10 to 25 mass %, or 15 to 25 mass %.

<Cured Product>

The resin precursor according to the present embodiment may be a cured product obtained by curing. The curing method may be photocuring or thermocuring depending on the characteristics of the curable composition to be contained. As the curing method, for example, a method of irradiating ultraviolet rays using an ultraviolet-curable composition may be employed.

As the physical properties of the cured product, the θgF value is preferably set to 0.5 or greater, more preferably 0.6 or greater, and furthermore preferably 0.7 or greater. The Abbe number ($v_d$) is preferably set to 10 or greater and 40 or smaller. In addition, both the θgF value and the Abbe number ($v_d$) preferably satisfy the aforementioned numeral ranges. Furthermore, the refractive index ($n_d$) with respect to the d-line may be set to 1.50 or higher and 1.65 or lower.

The refractive index of the optical material such as a glass material or an organic resin tends to decrease as the wavelength is shortened. As an index for indicating the wavelength dispersion of the refractive index, the θgF value or the Abbe number ($v_d$) is used. These values are unique to optical materials, but attempts for reducing the chromatic aberration have been made by appropriately combining optical materials having different dispersion characteristics in a dioptric system. However, when the configuration or the number of lenses is limited from the viewpoint of design requirements or the like, it may be difficult to sufficiently correct the chromatic aberration. In this regard, the cured product according to the present embodiment has a high θgF value and a unique dispersion characteristic. Since the cured product according to the present embodiment has such characteristics, it is possible to provide an excellent chromatic aberration correction function and solve such a problem.

The internal transmittance of the cured product is preferably set to 90% or higher over a wavelength range of 440 to 650 nm. According to the present embodiment, it is possible to provide a cured product having a high internal transmittance as the optical material.

<Optical Element/Optical System/Interchangeable Lens for Camera/Optical Device, etc>

The cured product according to the present embodiment can be used as an optical element. The optical element including such a cured product includes a mirror, a lens, a prism, a filter, or the like. Preferably, the cured product is used as an optical lens. In addition, the optical element according to the present embodiment may be used as an optical system including the optical element.

The optical system according to the present embodiment may be used as an interchangeable lens for camera including the optical system. For the optical element, the optical lens, and the interchangeable lens for camera, any configuration known in the art may be employed. In addition, the optical system according to the present embodiment may be used as an optical device including the optical system. The optical device including such an optical system is not particularly limited, but may include, for example, an imaging device such as a lens-interchangeable camera and a non-lens-interchangeable camera, an optical microscope, or the like.

(Imaging Device)

FIG. 1 is a perspective view illustrating an example in which the optical device according to the present embodiment is employed as an imaging device. An imaging device 1 is a so-called digital single-lens reflex camera (lens-interchangeable camera), and a photographing lens (optical system) 103 includes the cured product according to the present embodiment. A lens barrel 102 is detachably installed in a lens mount (not shown) of a camera body 101. In addition, the light passing through the lens 103 of the lens barrel 102 is focused on a sensor chip (solid-state image sensor) 104 of a multi-chip module 106 disposed on the back side of the camera body 101. The sensor chip 104 is a bare chip such as a so-called CMOS image sensor, and the multi-chip module 106 is, for example, a COG (chip on glass) type module in which the sensor chip 104 is mounted on a glass substrate 105 as a bare chip.

Figure 2A:
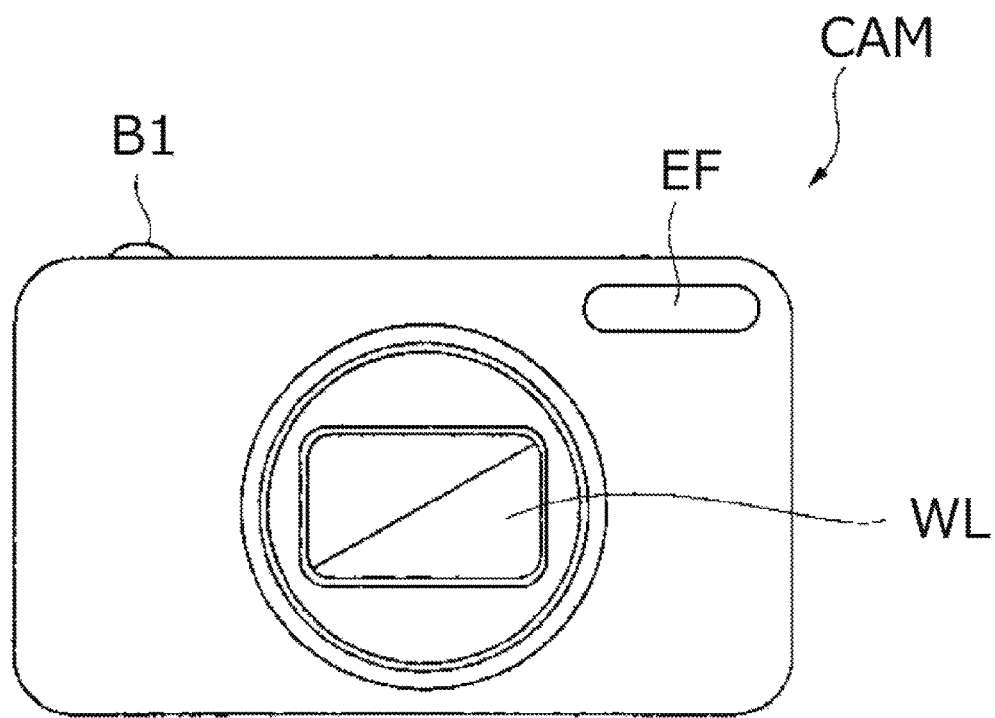
FIG. 2A and FIG. 2B are schematic diagrams illustrating another example in which an optical device according to the present embodiment is an imaging device.
Figure 2B:
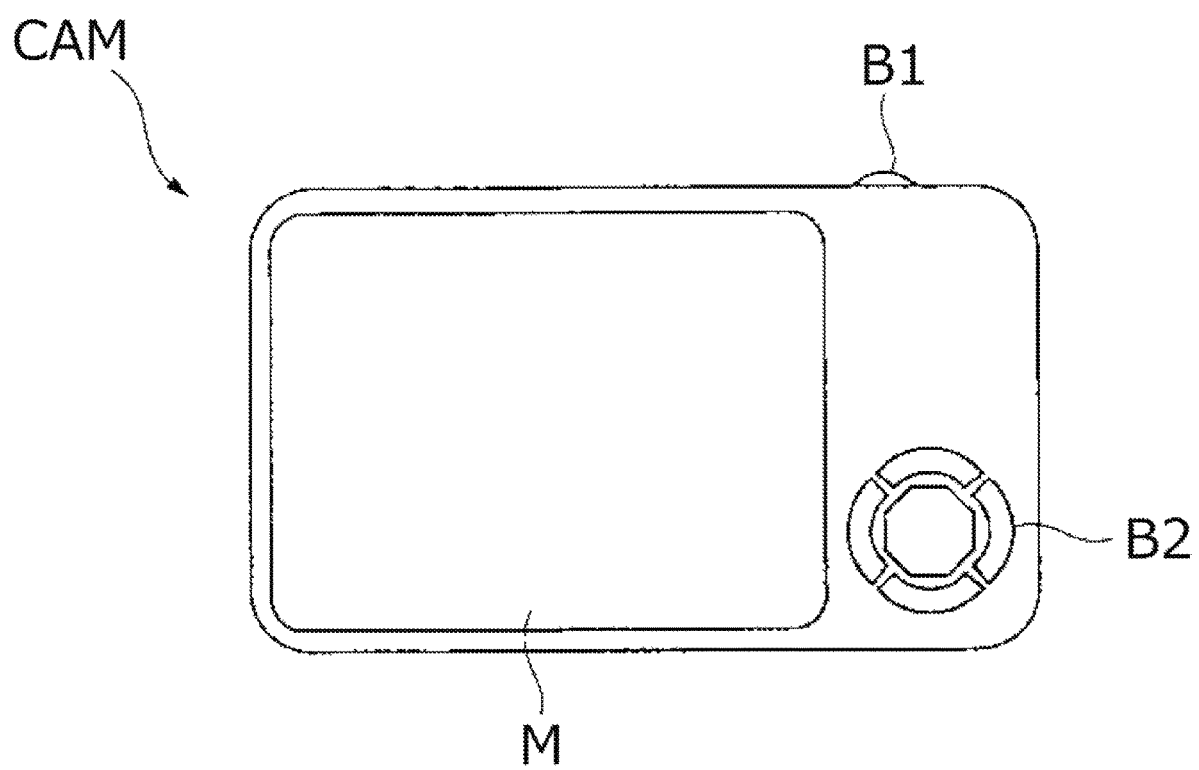

FIG. 2A and FIG. 2B are schematic diagrams illustrating another example in which the optical device according to the present embodiment is employed as an imaging device. FIG. 2A is a front view illustrating the imaging device CAM, and FIG. 2B is a rear view illustrating the imaging device CAM. The imaging device CAM is a so-called digital still camera (non-lens-interchangeable camera), and the photographing lens (optical system) WL includes the cured product according to the present embodiment. If a power button (not shown) of the imaging device CAM is pressed, a shutter (not shown) of the photographing lens WL is opened, and the light from a subject (object) is condensed by the photographing lens WL, and is focused on the image sensor arranged on the image plane. The subject image formed on the image sensor is displayed on a liquid crystal monitor M arranged on the rear of the imaging device CAM. A photographer determines the arrangement of the subject image while looking at the liquid crystal monitor M, and then presses down a release button B1 to capture the subject image with the image sensor and record and save the image in a memory (not shown). The imaging device CAM has an auxiliary light-emitting unit EF that emits auxiliary light when the subject is dark, a function button B2 used for setting various conditions of the imaging device CAM, or the like.

An optical system used in such a digital camera or the like is required to have higher resolution, lighter weight, and smaller size. In order to satisfy such requirements, it is effective to use an optical glass having a high refractive index in the optical system. From such a viewpoint, the optical glass according to the present embodiment is suitable as a member of such optical instrument. Note that the optical instrument applicable to the present embodiment is not limited to the imaging device described above, but may include, for example, a projector or the like. The optical element is not limited to a lens, but may include, for example, a prism or the like.

(Multi-Photon Microscope)

Figure 3:
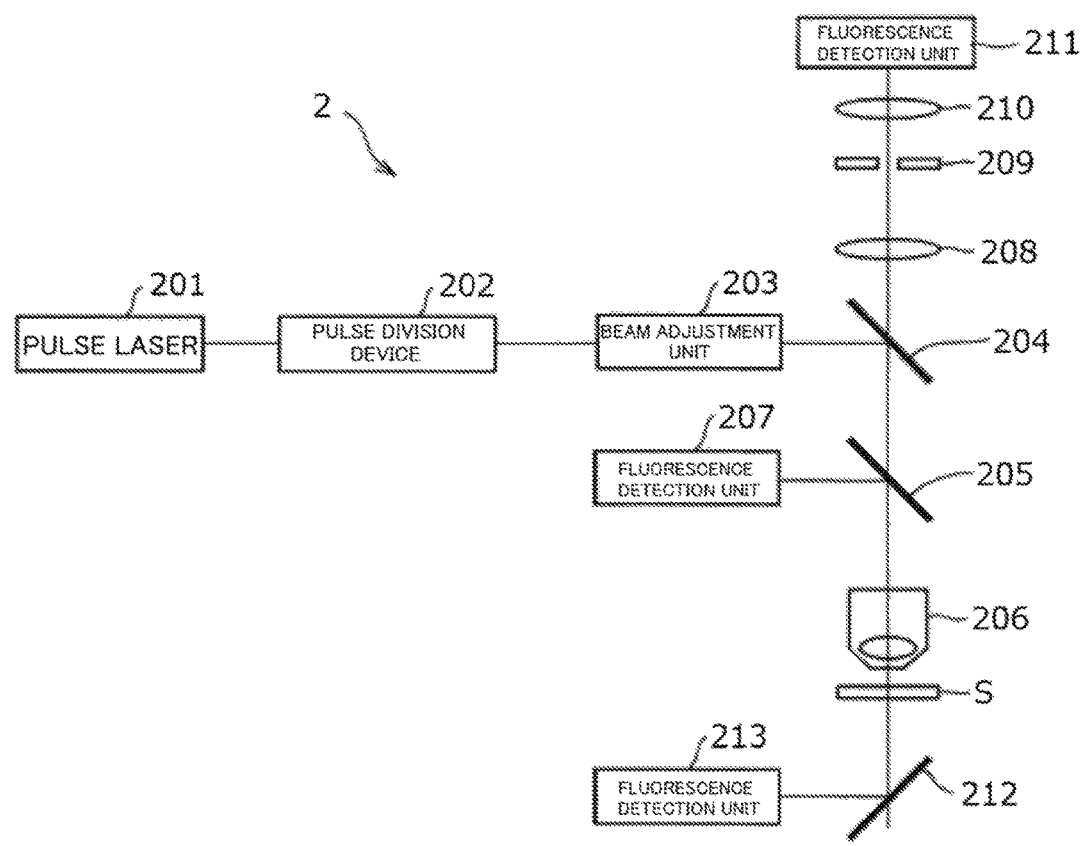
FIG. 3 is a block diagram illustrating an example in which an optical device according to the present embodiment is a multi-photon microscope.

FIG. 3 is a block diagram illustrating an example in which the optical device according to the present embodiment is employed as a multi-photon microscope. The multi-photon microscope 2 has an objective lens 206, a condensing lens 208, and a focusing lens 210 as optical elements. Hereinafter, the description will be focused on the optical system of the multi-photon microscope 2.

A pulse laser unit 201 emits, for example, ultrashort pulse light having a near-infrared wavelength (approximately 1,000 nm) and a pulse width of a femtosecond unit (for example, 100 femtoseconds). The ultrashort pulse light immediately after being emitted from the pulse laser unit 201 is generally linearly polarized light polarized in a predetermined direction.

A pulse division unit 202 divides the ultrashort pulse light and emits the ultrashort pulse light at a high repetition frequency.

The beam adjusting unit 203 has a function of adjusting the beam diameter of the ultrashort pulse light incident from the pulse division unit 202 depending on a pupil diameter of the objective lens 206, a function of adjusting convergence and divergence angles of the ultrashort pulse light in order to correct an axial chromatic aberration (focus difference) between the wavelength of the multiphoton excitation light emitted from a sample S and a wavelength of the ultrashort pulse light, and a pre-chirping function (group velocity dispersion compensation function) for applying an inverse group velocity dispersion to the ultrashort pulse light in order to correct the pulse width of the ultrashort pulse light spreading due to the group velocity dispersion while passing through the optical system, and the like.

The ultrashort pulse light emitted from the pulse laser unit 201 has a repetition frequency increasing by the pulse division unit 202, and the adjustment described above is performed by the beam adjustment unit 203. In addition, the ultrashort pulse light emitted from the beam adjusting unit 203 is reflected by a dichroic mirror 204 toward a dichroic mirror 205, passes through the dichroic mirror 205, is condensed by the objective lens 206, and is irradiated onto the sample S. In this case, a scanning means (not shown) may be used to scan the ultrashort pulse light onto an observation surface of the sample S.

For example, when fluorescence observation is performed for the sample S, fluorescent pigment where the sample S is stained is multiphoton-excited in the ultrashort pulse light irradiation area of the sample S and in the vicinity thereof, so that fluorescent light having a wavelength shorter than that of the ultrashort pulse light as an infrared wavelength (hereinafter, referred to as "observation light") is emitted.

The observation light emitted from the sample S to the objective lens 206 is collimated by the objective lens 206 and is reflected by the dichroic mirror 205 or transmits through the dichroic mirror 205 depending on its wavelength.

The observation light reflected by the dichroic mirror 205 enters a fluorescence detection unit 207. The fluorescence detection unit 207 includes, for example, a barrier filter, a PMT (photo multiplier tube), or the like, to receive the observation light reflected by the dichroic mirror 205 and output an electric signal depending on the light intensity. In addition, the fluorescence detection unit 207 detects the observation light over the observation surface of the sample S as the ultrashort pulse light is scanned onto the observation surface of the sample S.

Meanwhile, the observation light transmitting through the dichroic mirror 205 is de-scanned by a scanning means (not shown), transmits through the dichroic mirror 204, is condensed by the condensing lens 208, passes through a pin hole 209 provided in a position substantially conjugated with the focal position of the objective lens 206, transmits through the focusing lens 210, and enters the fluorescence detection unit 211.

The fluorescence detection unit 211 includes, for example, a barrier filter, a PMT, or the like to receive the observation light focused on the light-receiving surface of the fluorescence detection unit 211 by the focusing lens 210 and output an electric signal depending on the light intensity thereof. In addition, the fluorescence detection unit 211 detects the observation light over the observation surface of the sample S as the ultrashort pulse light is scanned onto the observation surface of the sample S.

Note that all of the observation light emitted from the sample S to the objective lens 206 may be detected by the fluorescence detection unit 211 by removing the dichroic mirror 205 from the optical path.

The observation light emitted from the sample S oppositely to the objective lens 206 is reflected by the dichroic mirror 212 and enters the fluorescence detection unit 213. The fluorescence detection unit 213 includes, for example, a barrier filter, a PMT, or the like to receive the observation light reflected by the dichroic mirror 212 and outputs an electric signal depending on the light intensity thereof. In addition, the fluorescence detection unit 213 detects the observation light over the observation surface of the sample S as the ultrashort pulse light is scanned onto the observation surface of the sample S.

The electric signals output from each of the fluorescence detection units 207, 211, and 213 may be input to, for example, a computer (not shown), and the computer may create an observation image on the basis of the input electric signals and display the created observation image or store data on the observation image.

<Cemented Lens and Production Method Thereof>

While the description has been focused on a case where the compound, the resin precursor, the cured product, and the like according to the present embodiment are used in a single-layer lens hereinbefore, the compound, the resin precursor, the cured product, and the like according to the present embodiment may also be suitably used as a bonding member of a cemented lens having a plurality of layers of lenses.

Figure 4:
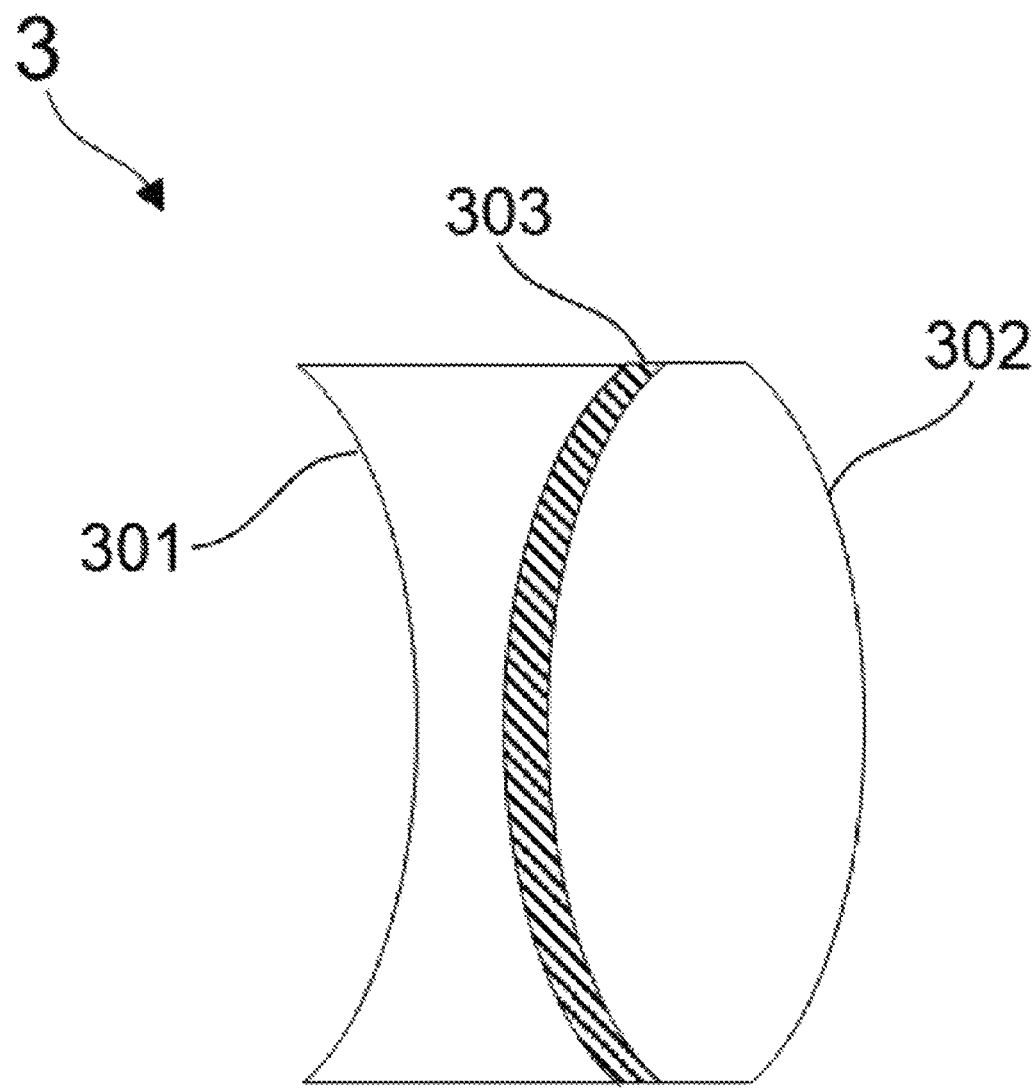
FIG. 4 is a schematic diagram illustrating an exemplary cemented lens according to the present embodiment.

FIG. 4 is a schematic diagram illustrating an example of a cemented lens according to the present embodiment. The cemented lens 3 is formed by bonding a first lens element 301 and a second lens element 302 by interposing a cured product 303 according to the present embodiment. Note that the lenses included in the cemented lens may also be referred to as "lens elements" as described above in order to clarify that the lenses are elements of the cemented lens. In this manner, the cured product 303 according to the present embodiment can function as the bonding member described above.

When the compound, the resin precursor, or the cured product according to the present embodiment is used in a cemented lens having two lens elements, a production method may include, first, (1) an adjoining step of adjoining the first lens element and the second lens element by interposing the resin precursor according to the present embodiment, and (2) a bonding step of bonding the first lens element and the second lens element by curing the resin precursor.

In the (1) adjoining step, the resin precursor according to the present embodiment is interposed between the first lens element and the second lens element in an uncured state. For example, when the resin precursor is a liquid composition, the resin precursor is applied to contact surfaces of the first lens element and the second lens element, and the two lens elements are overlapped.

In the (2) bonding step, the method of curing the resin precursor may be either photocurable or thermocurable. However, the resin precursor is preferably cured by irradiating light onto the resin precursor. This light is preferably irradiated onto the resin precursor through the first or second lens element. The compound, the resin precursor, and the cured product according to the present embodiment can suppress yellowing caused by aging and maintain high transparency for a long period of time. This production method is preferable due to such reasons.

The cemented lens obtained in this manner may be used in an optical system, as described above in conjunction with the single-layer lens. In addition, the cemented lens according to the present embodiment may be used as an interchangeable lens for camera or an optical device having an optical system, as described above in conjunction with the single-layer lens. Note that, although a cemented lens using two lens elements has been described in the aforementioned embodiment, the present invention may also be applied to a cemented lens having three or more lens elements without limiting thereto. In addition, in the case of the cemented lens having three or more lens elements, the cured product according to the present embodiment may be used in all of the bonding members between the lens elements. However, without limiting thereto, at least one of the bonding members may be the cured product according to the present embodiment.

EXAMPLES

While the present invention will be described in more detail with reference to the following Examples and Comparative Examples, the present invention is not limited to the following Examples. First, a compound was synthesized, a resin precursor containing the compound and a cured product thereof were prepared, and the physical properties were evaluated for each of them.

I. Production of Compound and Physical Property Evaluation

Example 1 (Synthesis of Compound (1A))

(Synthesis of Intermediate Compound (a1))

Under an argon gas flow, 3-formyl-4-methoxyphenylboronic acid of 10.00 g (55.6 mmol), tetrahydrofuran (THF, dehydrated) of 50 mL, and ethanol (dehydrated) of 50 mL were weighed into a reaction vessel of 300 mL and were stirred at 0° C. Sodium borohydride (NaBH$_4$) of 1.36 g (36.0 mmol) was added thereto little by little. After stirring at 0° C. for 2 hours, the reaction was checked by TLC to know whether or not the raw materials had disappeared. When city water of 50 mL was added thereto to stop the reaction, a white precipitate was immediately formed.

Then, the suspension was filtered under reduced pressure to remove the organic solvent. Hydrochloric acid having a concentration of 2 mol/L was added until the suspension became neutral. Then, the precipitate was collected by filtration. The filtered product was washed with ethyl acetate of 50 mL and was dried at 40° C. under reduced pressure to obtain an intermediate compound (a1) ((3-hydroxymethyl)-4-methoxy-phenyl) boronic acid) as the filtered product. The amount was 9.27 g (50.9 mmol), and the yield was 91.5%.

[Chemical Expression 9]

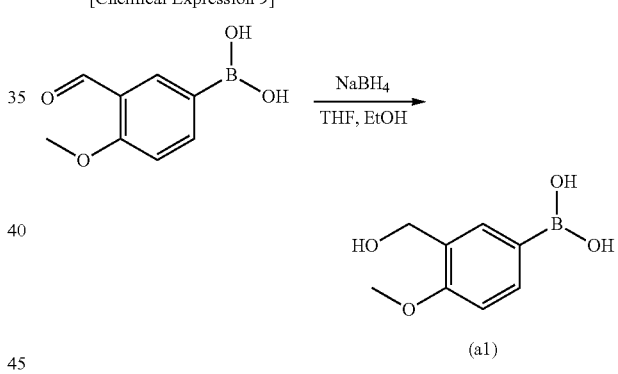

(Synthesis of Intermediate Compound (a2))

4,4'-dichlorobenzophenone of 3.30 g (12.5 mmol), the intermediate compound (a1) of 5.00 g (27.5 mmol), sodium hydrogen carbonate of 3.57 g (42.5 mmol), 1,4-dioxane of 150 mL, and distilled water of 75 mL were weighed into a reaction vessel of 500 mL, and argon bubbling was performed while stirring at the room temperature. After stirring for 30 minutes, tetrakis (triphenylphosphine) palladium (Pd (Ph$_3$)$_4$) of 0.29 g (0.25 mmol) was added to the reaction system. In addition, the argon bubbling was switched to the argon gas flow, and stirring was performed at 90° C. overnight. Then, the reaction was checked by TLC to know whether or not the raw materials had disappeared, and the heating was stopped. After cooling the reaction solution to the room temperature, a saturated ammonium chloride aqueous solution of 25 mL and city water of 150 mL were added. Then, the mixture was stirred for 30 minutes. The deposited precipitate was collected by filtration and was washed with water of 300 mL, so that yellow-white powder was obtained.

The obtained yellow-white powder was dried under reduced pressure at 70° C. overnight. A mixed solution (tetrahydrofuran:chloroform=1:9) of 900 mL was added to the powder, and the mixture was heated at 60° C. This solution was purified by a silica gel column with a developing solvent (tetrahydrofuran:chloroform=1:9) to obtain a yellow-white solid. The amount was 4.86 g (10.7 mmol), and the yield was 85.6%.

[Chemical Expression 10]

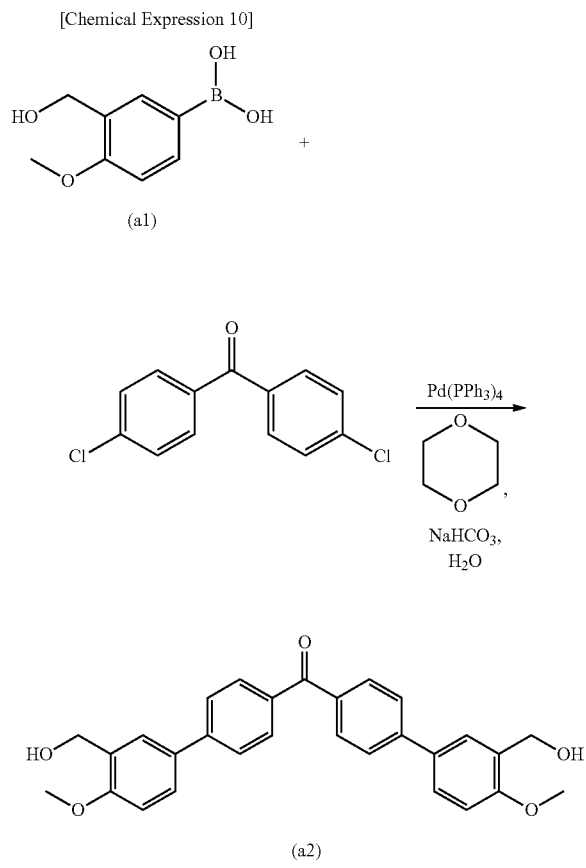

(Synthesis of Intermediate Compound (a3))

Under an argon gas flow, the intermediate compound (a2) of 2 g (4.40 mmol) and dichloromethane (dehydrated) of 80 mL were weighed into a reaction vessel of 200 mL, and cooling was performed at 0° C. Phosphorus tribromide ($PBr_3$) of 1.01 g (3.74 mmol) was added dropwise thereto for 5 minutes, and heating was performed to the room temperature. After stirring for 3 hours, the reaction was checked by TLC and HPLC analysis to know whether or not the raw materials had disappeared, and the stirring was stopped. City water of 80 mL at a temperature of 10° C. or lower was added thereto, and stirring was further performed for 30 minutes. The deposited precipitate was collected by filtration, and the filtrate was then separated into an organic layer and an aqueous layer. The organic components dissolved in the aqueous layer were recovered by washing the aqueous layer twice with dichloromethane of 50 mL. Subsequently, the organic components collected from the organic layer and the aqueous layer were mixed to form a mixed solution. The mixed solution was suctioned and filtrated. Note that, since water may freeze or filtration may stop when performing suction and filtration, the operation was performed while warming from the top of the funnel.

The obtained filtrate was vacuum-concentrated, and the filtrate was added again. Then, they were suspended by adding tetrahydrofuran of 50 mL to obtain a suspension. City water of 200 mL was added to the obtained suspension, and the deposited precipitate was collected by filtration. The filtrate was washed with city water until the filtrate became neutral. Then, washing was further performed with methanol of 20 mL. A target product was obtained by drying the obtained white powder under reduced pressure at 70° C. overnight. The amount was 2.36 g (4.07 mmol), and the yield was 92.5%.

[Chemical Expression 11]

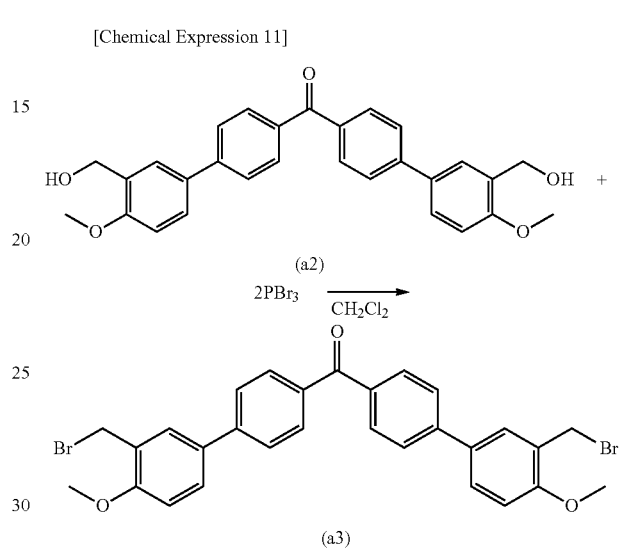

(Synthesis of Intermediate Compound (a4))

Tetrahydrofuran (dehydrated) of 25 mL and sodium hydride (60% concentration) of 0.47 g (11.7 mmol) were weighed and placed in a reaction vessel of 100 mL under an argon gas flow, and cooling was performed at 0° C. A diluted solution of 2,2-dimethyl-1,3-propanediol of 2.98 g (28.6 mmol) and tetrahydrofuran of 5 mL was added thereto dropwise over 15 minutes, and heating was performed to the room temperature. After stirring for one hour, the intermediate compound (a3) of 1.6 g was added at once, and the mixture was stirred at 60° C. for 16 hours. Then, the reaction was checked by TLC and HPLC analysis to know whether or not the raw materials had disappeared. City water of 30 mL was added thereto, and the reaction was stopped. Subsequently, an organic layer and an aqueous layer were separated by adding ethyl acetate of 100 mL to the reaction solution. The organic components dissolved in the aqueous layer were recovered by washing the aqueous layer twice with ethyl acetate of 30 mL. Then, the organic components recovered from the organic layer and the aqueous layer were mixed to form a mixed solution. The obtained mixed solution was washed with water and saturated saline in this order, and was then dried with magnesium sulfate.

Then, the solvent was distilled off by vacuum-concentrating the dried mixed solution to obtain a pale yellow solid of 4.21 g. The solid was purified by a silica gel column with a developing solvent (ethyl acetate:chloroform=1:4) to obtain a white solid. The obtained white solid was dried under reduced pressure at 70° C. for one hour. The amount was 1.54 g (2.46 mmol), and the yield was 71.3%.

[Chemical Expression 12]

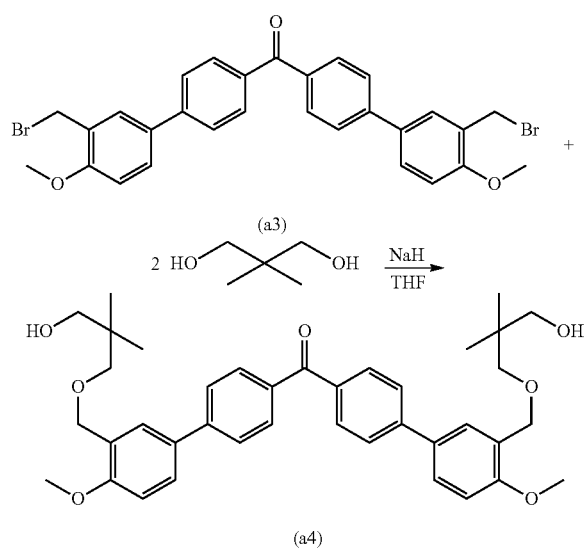

(Synthesis of Target Compound (1A))

The intermediate compound (a4) of 1.50 g (2.39 mmol), chloroform (dehydrated) of 12 mL, triethylamine (TEA) of 2.30 g (22.7 mmol), and p-methoxyphenol of 6.0 mg (48 µmol) were weighed and placed in a reaction vessel of 30 mL under an argon gas flow, and cooling was performed at 0° C. When methacryloyl chloride of 0.85 g (8.13 mmol) was added dropwise thereto over 5 minutes, the solution color changed to pink, and triethylamine hydrochloride was precipitated. Subsequently, the heating was performed from 0° C. to the room temperature, and the solution was stirred for one hour. Then, the reaction was checked by TLC and HPLC analysis to know whether or not the raw materials had disappeared. The reaction was stopped by adding city water of 6 mL thereto. Subsequently, the reaction solution was separated into an organic layer and an aqueous layer. The organic components dissolved in the aqueous layer were recovered by washing the aqueous layer twice with chloroform of 30 mL. In addition, the organic components recovered from the organic layer and the aqueous layer were mixed to form a mixed solution. The mixed solution was washed with water and saturated saline in this order, and was then dried with sodium sulfate.

Then, p-methoxyphenol of 6.0 mg (48 µmol) and toluene of 10 mL were added to the dried mixed solution. In addition, the mixed solution was vacuum-concentrated to distill off triethylamine and the solvent, so that a crude product of 2.80 g was obtained. The obtained crude product was purified by a silica gel column with a developing solvent (chloroform).

A chloroform solution of p-methoxyphenol of 0.9 mg (corresponding to 500 ppm) was added to a fraction of the silica gel column obtained in the previous process, and the mixture was vacuum-concentrated at 30° C. or lower, so that a yellow-white solid as a target substance was obtained. In the concentration process, the mixture was not kept under the reduced pressure for a long time to prevent polymerization. The amount was 1.73 g (2.27 mmol), and the yield was 94.9%.

[Chemical Expression 13]

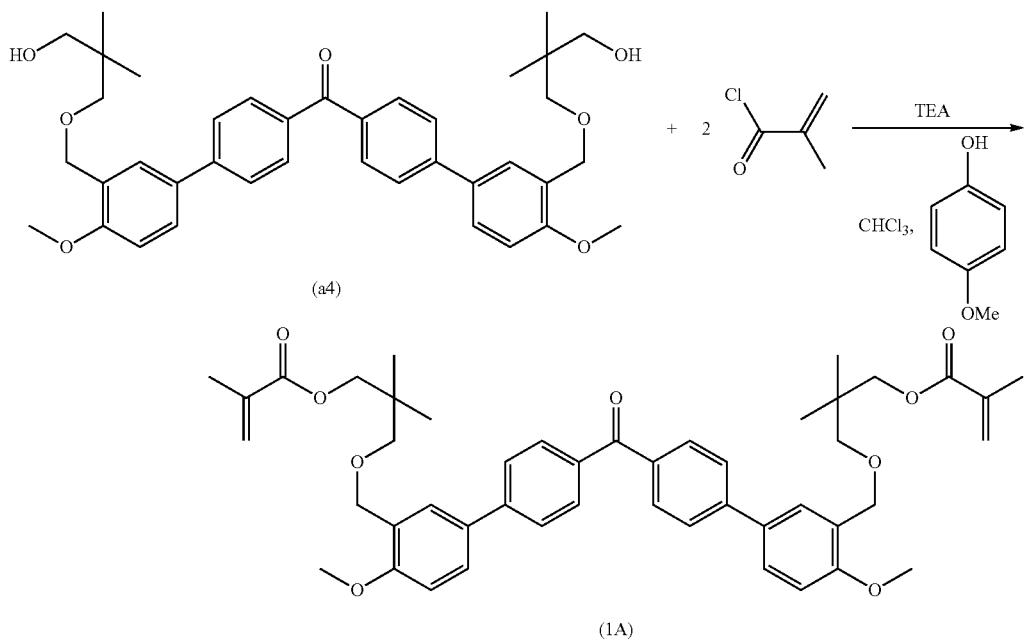

The measurement results of $^1$H-NMR ("JNM-AL300" manufactured by JEOL Ltd.) of the compound (1A) are shown below.

$^1$H-NMR (300 MHz, DMSO-d6): δ0.95 (12H, s), 1.81 and 1.85 (6H, s), 3.31 (4H, s), 3.84 (6H, s), 3.94 (4H, s), 4.54 (4H, s), 5.59 and 5.97 (4H, s), 7.11-7.14 (2H, d), 7.69-7.86 (12H, m)

m.p.=100° C.

Example 2 (Synthesis of Compound (1B))

(Synthesis of Intermediate Compound (b4))

The intermediate compound (b4) was synthesized using the intermediate compound (a3) synthesized in Example 1. Under an argon gas atmosphere, tetrahydrofuran (dehydrated) of 300 mL and sodium hydride (60% concentration) of 2.33 g (58.5 mmol) were weighed and placed in a reaction vessel of 1000 mL, and cooling was performed with ice. A solution of ethylene glycol of 12.8 g (206 mmol) with tetrahydrofuran of 100 mL was added thereto dropwise, and heating was performed to the room temperature. After stirring for one hour, the intermediate compound (a3) of 10 g (17.2 mmol) was added at once, and the mixture was heated to 60° C. After heating and stirring overnight, the reaction was checked by TLC to know whether or not the raw materials had disappeared. The reaction was stopped by adding city water of 400 mL thereto. The reaction solution was separated into an organic layer and an aqueous layer by adding ethyl acetate of 400 mL thereto. The organic components were recovered from the aqueous layer by washing the aqueous layer twice with ethyl acetate of 200 mL. In addition, the organic components recovered from the organic layer and the aqueous layer were mixed to obtain a mixed solution. The obtained mixed solution was washed with water and saturated saline in this order and was then dried with magnesium sulfate.

Then, the solvent was distilled off by vacuum-concentrating the dried mixed solution to obtain a pale yellow solid of 11.3 g. The solid was purified by an NH gel column (developed with chloroform) to obtain a white solid. The obtained white solid was dried under reduced pressure at 80° C. overnight. The amount was 5.01 g (9.23 mmol), and the yield was 53.7%.

[Chemical Expression 14]

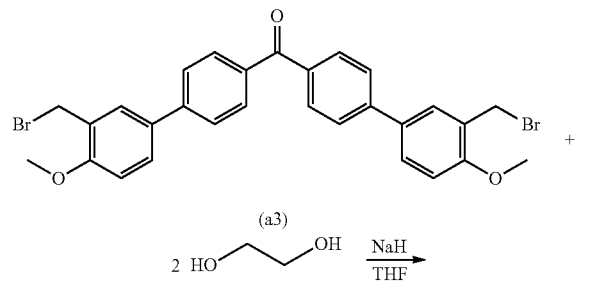

(a3)

2 HO~~~OH  NaH / THF

[Chemical Expression 15]

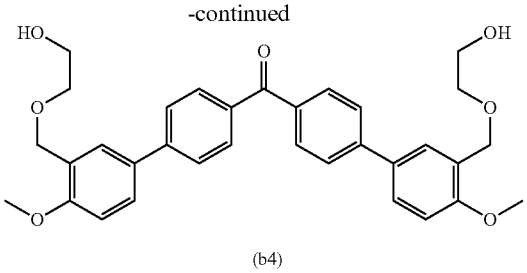

(b4)

(Synthesis of Target Compound (1B))

The aforementioned processes were repeated to obtain a total of 10.7 g of the intermediate compound (b4), and then, the intermediate compound (b4) of 10.7 g, chloroform (dehydrated) of 90 mL, triethylamine of 18.9 g (187 mmol), and p-methoxyphenol of 49.0 mg (395 μmol) were weighed and placed in a reaction vessel of 200 mL under an argon gas flow, and cooling was performed at 0° C. When methacryloyl chloride of 7.00 g (67.0 mmol) was added dropwise thereto for 5 minutes, the solution color changed to pink, and triethylamine hydrochloride was precipitated. Subsequently, heating was performed from 0° C. to the room temperature, and stirring was performed for one hour. Then, the reaction was checked by TLC and HPLC analysis to know whether or not the raw materials had disappeared. The reaction was stopped by adding city water of 200 mL thereto. Subsequently, the reaction solution was separated into an organic layer and an aqueous layer. The organic components dissolved in the aqueous layer were recovered by washing the aqueous layer twice with chloroform of 60 mL. The organic components recovered from the obtained organic layer and the aqueous layer were mixed to obtain a mixed solution. The mixed solution was washed with water and saturated saline in this order, and was then dried with sodium sulfate.

Then, p-methoxyphenol of 49.0 mg (395 mmol) and toluene of 20 mL were added to the dried mixing container. In addition, the mixed solution was vacuum-concentrated to distill off triethylamine and the solvent, so that a crude product of 17.0 g was obtained. The obtained crude product was purified by a silica gel column with a developing solvent (ethyl acetate:toluene=1:10).

A chloroform solution of p-methoxyphenol of 49.0 mg (395 μmol) was added to a fraction of the silica gel column obtained in the previous process, and the mixture was vacuum-concentrated at 30° C. or lower to obtain a concentrate. In addition, the obtained concentrate was washed with diethyl ether and was collected by filtration, and the obtained filtrate was dissolved in chloroform. A chloroform solution of p-methoxyphenol of 5.2 mg (corresponding to 500 ppm) was further added thereto, and the solvent was distilled off by vacuum-concentrating the solution at 30° C. or lower to obtain a milky solid as a target substance. The amount was 10.4 g (15.3 mmol), and the yield was 77.6%.

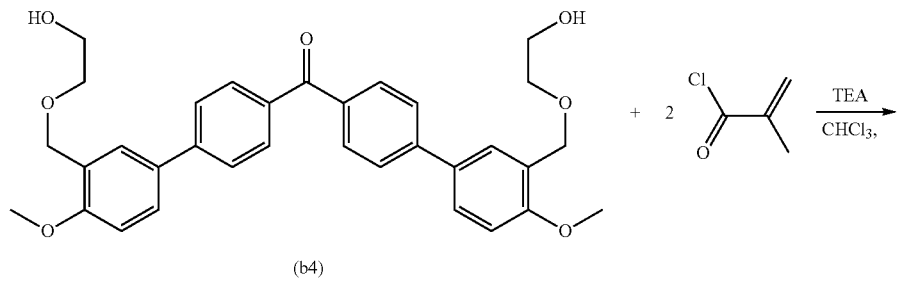

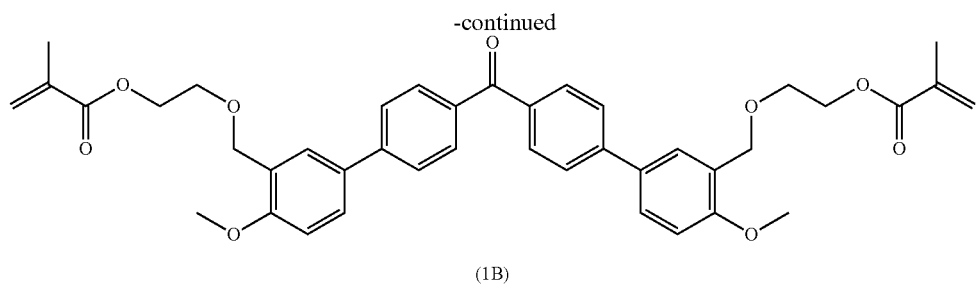

(1B)

The measurement results of $^1$H-NMR ("JNM-AL300" manufactured by JEOL Ltd.) of the compound (1B) are shown below.

$^1$H-NMR (300 MHz, DMSO-d6): δ1.86 (6H, s), 3.76 (4H, t), 3.86 (6H, s), 4.30 (4H, t), 4.61 (4H, s), 5.65 and 6.03 (4H, s), 7.13-7.15 (2H, d), 7.71-7.83 (12H, m)

m.p.=80° C.

<Evaluation of Physical Properties of Compound>

(Preparation of Refractive Index Measurement Sample)

The obtained compound was heated and melted to obtain a liquid state, and was then solidified by cooling to obtain a refractive index measurement sample.

(Measurement and Evaluation)

The refractive index was measured using a multi-wavelength refractometer (manufactured by Anton Paar Japan). Refractive indices $n_C$, $n_d$, $n_F$, and $n_g$ were measured for the C-line (wavelength: 656.3 nm), the d-line (587.6 nm), the F-line (486.1 nm), and the g-line (435.8 nm), respectively. In addition, the θgF value and the $ν_d$ value were calculated from the following equations.

$$θgF=(n_g-n_F)/(n_F-n_C)$$

$$ν_d=(n_d-1)/(n_F-n_C)$$

TABLE 1

| Name of compound | Example 1 1A | Example 2 1B |
|---|---|---|
| $n_c$ | 1.5916 | 1.6091 |
| $n_d$ | 1.6016 | 1.6191 |
| $n_F$ | 1.6272 | 1.6477 |
| $n_g$ | 1.6556 | 1.6782 |
| $θ_gF$ | 0.798 | 0.790 |
| $ν_d$ | 16.9 | 16.0 |

II. Production of Resin Precursor and Physical Property Evaluation

Example 3

The compound (1A) was mixed with the components of the curable composition at the ratios shown in Table 2 to produce a resin precursor (1A-1). The obtained resin precursor was in a solution state under a normal temperature and a normal pressure. Note that the mixing ratios in the table are based on mass % unless specified otherwise.

Examples 4 to 6

Each resin precursor was produced in the same manner as in Example 3 except that the components were mixed at the ratios shown in Table 2. The states of each resin precursor were checked under a normal temperature and a normal pressure.

The components used as the curable composition are shown.

Main agent 1

9,9-bis[4-(2-acryloyloxyethoxy)phenyl]fluorene (Formula (i))

[Chemical Expression 16]

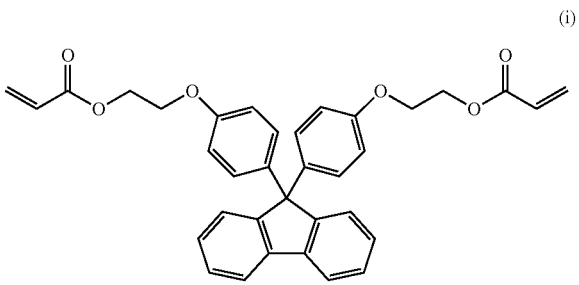

(i)

Main agent 2

1,6-di(meth)acryloyloxy-2,2,3,3,4,4,5,5-octafluoro-hexane (Formula (ii))

[Chemical Expression 17]

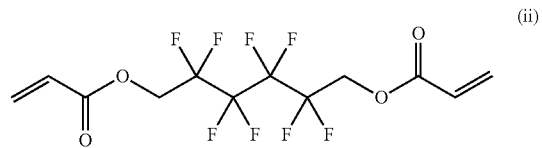

(ii)

Main agent 3

1,6-hexanediol diacrylate(AHDN) (Formula (iii))

[Chemical Expression 18]

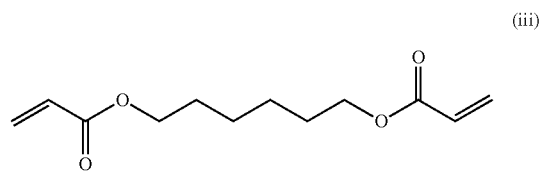

(iii)

Compatibilizer methoxytripropylene glycol acrylate (Formula (iv))

[Chemical Expression 19]

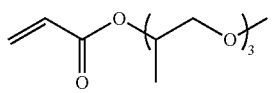
(iv)

Photopolymerization initiator 1:

1-hydroxy-cyclohexyl-phenyl-ketone (Formula (v))

[Chemical Expression 20]

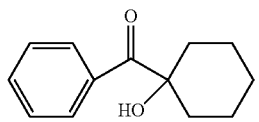
(v)

Photopolymerization initiator 2:

bis(2-4-6-trimethylbenzoyl)-phenylphosphine oxide (Formula (vi))

[Chemical Expression 21]

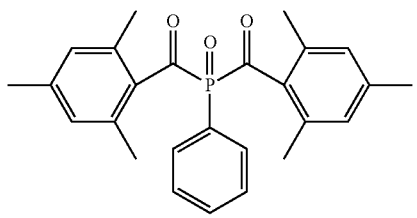
(vi)

Radical scavenger:

bis(1,2,2,6,6-pentamethyl-4-biperidyl)sebacate (Formula (vii))+methyl 1,2,2,6,6-pentamethyl-4-piperidyl sebacate (Formula (viii)

[Chemical Expression 22]

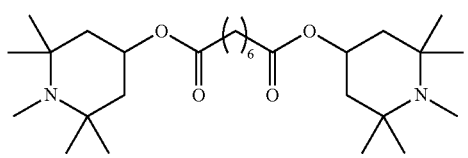
(vii)

[Chemical Expression 23]

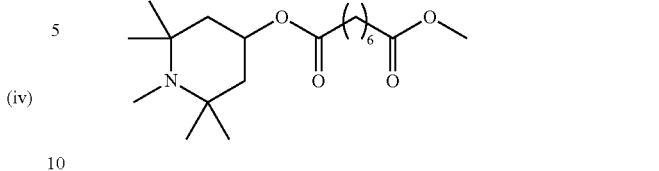
(viii)

Ultraviolet absorber:

2-(2-hydroxy-5-t-octylphenyl)-2H-benzotriazole (Formula (ix))

[Chemical Expression 24]

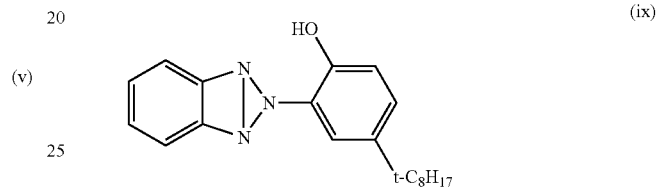
(ix)

<Physical Property Evaluation of Resin Precursor>
(Preparation of Refractive Index Measurement Sample)
The physical properties of the resin precursor were measured in a liquid state without curing the resin precursor.
(Measurement and Evaluation)
The refractive indices $n_C$, $n_d$, $n_F$, and $n_g$ of each resin precursor were measured in the same manner as in the measurement of the physical properties of the compound, and the θgF value and the $v_d$ value were calculated.

TABLE 2

| Name of resin precursor | Eample 3<br>1A-1 | Example 4<br>1A-2 | Example 5<br>1A-3 | Example 6<br>1B-1 |
|---|---|---|---|---|
| Compound (1A) | 20 | 18.5 | 35 | |
| Compound (1B) | | | | 20 |
| Main agent 1 (Compound (i)) | 30.4 | 26.7 | 26 | 30.4 |
| Main agent 2 (Compound (ii)) | 41.4 | 36.4 | | 41.4 |
| Main agent 3 (Compound (iii)) | | 11.2 | 35.8 | |
| Compatibilizer (Compound (iv)) | 3.2 | 2.8 | 3.2 | 3.2 |
| Photopolymerization initiator 1 (Compound (v)) | 1.6 | 1.4 | | 1.6 |
| Photopolymerization initiator 2 (Compound (vi)) | 0.2 | 0.2 | | 0.2 |
| Radical scavenger (Compound (vii) + (viii)) | 1.6 | 1.4 | | 1.6 |
| Ultraviolet absorber (Compound (ix)) | 1.6 | 1.4 | | 1.6 |
| Total (mass %) | 100 | 100 | 100 | 100 |
| State under under normal temperature and normal pressure | Liquid | Liquid | Liquid | Liquid |
| $n_c$ | 1.5153 | 1.5075 | 1.5313 | 1.5187 |
| $n_d$ | 1.5207 | 1.5122 | 1.5368 | 1.5242 |
| $n_F$ | 1.5351 | 1.5263 | 1.5524 | 1.5391 |

TABLE 2-continued

| Name of resin precursor | Eample 3 1A-1 | Example 4 1A-2 | Example 5 1A-3 | Example 6 1B-1 |
|---|---|---|---|---|
| $n_g$ | 1.5489 | 1.5393 | 1.5660 | 1.5536 |
| $\theta_g F$ | 0.697 | 0.691 | 0.640 | 0.711 |
| $v_d$ | 26.3 | 27.2 | 25.4 | 25.7 |

III. Production of Cured Product and Physical Property Evaluation

Example 7

The resin precursor (1A-1) was interposed between synthetic quartz (t=1 mm) and was irradiated with light from a high-intensity mercury-xenon lamp ("LC8", manufactured by Hamamatsu Photonics KK) by nipping a wavelength cutoff filter of 385 nm or shorter to obtain a cured product (1A-1).

Examples 8 to 10

Each cured product was obtained in the same manner as in Example 7 except that the resin precursors shown in Table 3 were used. The states of each cured product were checked under a normal temperature and a normal pressure.
<Physical Property Evaluation of Cured Product>
(Preparation of Refractive Index Measurement Sample)
A silicon rubber sheet having a rectangular opening was placed on a quartz glass substrate, and the opening was filled with the resin precursor and was then covered with a quartz glass substrate. Then, the resin precursor was irradiated with ultraviolet rays by interposing a quartz glass substrate for curing. In addition, the cured product was released from the mold to obtain a refractive index measurement sample having a shape of 15 mm by 15 mm and a thickness of 0.5 mm.
(Measurement and Evaluation)
The refractive indices $n_C$, $n_d$, $n_F$, and $n_g$ were measured in the same manner as in the physical property measurement of the compound, and the θgF value and the Abbe number ($v_d$ value) were calculated.

TABLE 3

| Name of cured product | Example 7 1A-1 | Example 8 1A-2 | Example 9 1A-3 | Example 10 1B-1 |
|---|---|---|---|---|
| $n_c$ | 1.5428 | 1.5397 | 1.5620 | 1.5451 |
| $n_d$ | 1.5484 | 1.5446 | 1.5680 | 1.5507 |
| $n_F$ | 1.5632 | 1.5578 | 1.5830 | 1.5654 |
| $n_g$ | 1.5782 | 1.5707 | 1.5970 | 1.5798 |
| $\theta_g F$ | 0.735 | 0.713 | 0.670 | 0.709 |
| $v_d$ | 26.9 | 30.1 | 27.0 | 27.1 |

Through the aforementioned measurement, it was recognized that the cured product obtained from the compounds of the examples and the resin precursors containing the same have a high θgF value and a low refractive index dispersion characteristic ($v_d$ value).

Examples 11 to 13

For the cured products 1A-1 and 1A-2 using the curable composition containing the acrylate-based main agent, the internal transmittance kept for 27 days from the curing was measured.

(Preparation of Transmittance Measurement Sample)
A sample having a thickness of 0.5 mm and a sample having a thickness of 1.0 mm for each cured product were prepared as transmittance measurement samples in the same manner as the aforementioned method of preparing the refractive index measurement sample. In addition, the resin precursor kept for 27 days from the curing was provided for the measurement.
(Evaluation of Internal Transmittance)
The transmittance was measured for each of the sample thicknesses of 0.5 mm and 1.0 mm, and was corrected on the basis of the following equation. In the measurement, a spectrophotometer ("UV-4700" manufactured by Shimadzu Corporation) was used.

Internal transmittance (%)=$(A/B)^{[100/(a-b)]} \times 100$

A: transmittance of thickness of 1.0 mm
B: transmittance of thickness of 0.5 mm
a: actual measurement thickness of 1.0 mm thick sample
b: actual measurement thickness of 0.5 mm thick sample
*Internal transmittance conversion data of 0.5 mm
Table 4 shows the results of the internal transmittance (%) at each wavelength in Examples 11 to 13.

TABLE 4

| Name of cured product | Example 11 1A-1 | Example 12 1A-2 | Example 13 1B-1 |
|---|---|---|---|
| 420 nm | 88% | 85% | 86% |
| 440 nm | 96% | 94% | 95% |
| 460 nm | 98% | 97% | 98% |
| 480 nm | 99% | 98% | 99% |
| 500 nm | 99% | 99% | 99% |
| 550 nm | 100% | 100% | 100% |
| 600 nm | 100% | 100% | 100% |
| 650 nm | 100% | 100% | 100% |

1 imaging device (lens-interchangeable camera),
101 camera body,
102 lens barrel,
103 lens,
104 sensor chip,
105 glass substrate,
106 multi-chip module,
CAM imaging device (non-lens-interchangeable camera),
WL photographing lens,
M liquid crystal monitor,
EF auxiliary light-emitting unit,
B1 release button,
B2 function button,
2 multi-photon microscope,
201 pulse laser unit,
202 pulse division unit,
203 beam adjusting unit,
204, 205, 212 dichroic mirror,
206 objective lens,
207, 211, 213 fluorescence detection unit,
208 condensing lens,
209 pin hole,
210 focusing lens,
S sample,
3 cemented lens,
301 first lens element,
302 second lens element,
303 cured product

What is claimed is:

1. A compound expressed in the following formula (1)

[Chemical Expression 1]

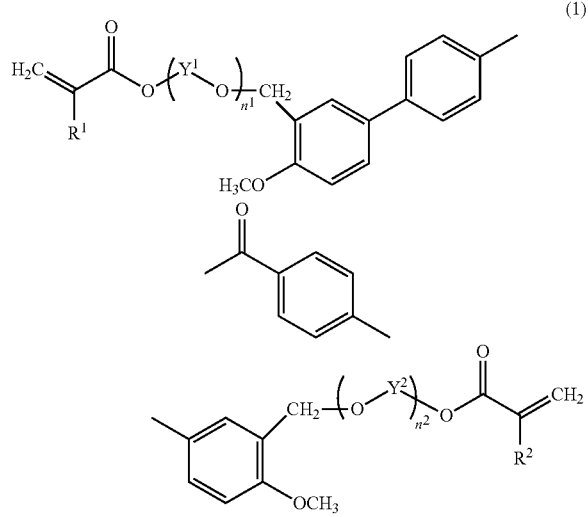

(where $R^1$ and $R^2$ independently denote a hydrogen atom or a methyl group, $Y^1$ and $Y^2$ independently denote an alkylene group having a carbon number of 1 to 9, and $n^1$ and $n^2$ independently denote an integer of 0 to 3).

2. A resin precursor comprising:
the compound according to claim 1; and
a curable composition.

3. The resin precursor according to claim 2, wherein the curable composition is a photocurable composition.

4. The resin precursor according to claim 2, wherein the curable composition includes at least one selected from a group consisting of a fluorine-containing acrylate compound, a fluorine-containing methacrylate compound, an acrylate compound having a fluorene structure, a methacrylate compound having a fluorene structure, a diacrylate compound, and a dimethacrylate compound.

5. The resin precursor according to claim 2, wherein the curable composition includes at least one selected from a group consisting of 1,6-di(meth)acryloyloxy-2,2,3,3,4,4,5,5-octafluorohexane, 9,9-bis[4-(2-acryloyloxyethoxy)phenyl]fluorene, and 1,6-hexanediol diacrylate.

6. The resin precursor according to claim 2, wherein a content of the compound is 10 to 50 mass %.

7. A cured product obtained by curing the resin precursor according to claim 2.

8. The cured product according to claim 7, wherein a θgF value is set to 0.5 or greater.

9. The cured product according to claim 7, wherein a refractive index ($n_d$) for a d-line is set to 1.50 or higher and 1.65 or lower.

10. The cured product according to claim 7, wherein an Abbe number ($v_d$) is set to 10 or greater and 40 or smaller.

11. The cured product according to claim 7, wherein an internal transmittance is 90% or higher over a wavelength range of 440 to 650 nm.

12. An optical element obtained by using the cured product according to claim 7.

13. An optical system comprising the optical element according to claim 12.

14. An interchangeable lens for camera comprising the optical system according to claim 13.

15. An optical device comprising the optical system according to claim 13.

16. A cemented lens comprising a first lens element and a second lens element bonded by interposing the cured product according to claim 7.

17. An optical system comprising the cemented lens according to claim 16.

18. An interchangeable lens for camera comprising the optical system according to claim 17.

19. An optical device comprising the optical system according to claim 17.

20. A production method for cemented lens, comprising:
an adjoining step of adjoining a first lens element and a second lens element by interposing the resin precursor according to claim 2; and
a bonding step of bonding the first lens element and the second lens element by curing the resin precursor.

21. The production method for cemented lens according to claim 20, wherein,
in the bonding step, the resin precursor is cured by receiving an irradiated light.

22. The production method for cemented lens according to claim 21, wherein
the light is irradiated onto the resin precursor through the first lens element.

23. The production method for cemented lens according to claim 21, wherein
the light is irradiated onto the resin precursor through the second lens element.

* * * * *